(12) United States Patent
Jam (10) Patent No.: US 7,478,634 B2
(45) Date of Patent: Jan. 20, 2009

(54) RESPIRATORY BOOSTER MACHINE AND METHOD FOR ENHANCING VENTILATION

(76) Inventor: Mohammad R. Jam, 481 W. Audubon Dr., #229, Fresno, CA (US) 93711

( * ) Notice: Subject to any disclaimer, the term of this patent is extended or adjusted under 35 U.S.C. 154(b) by 1129 days.

(21) Appl. No.: 10/654,816

(22) Filed: Sep. 3, 2003

(65) Prior Publication Data

US 2004/0069304 A1    Apr. 15, 2004

Related U.S. Application Data

(60) Provisional application No. 60/411,167, filed on Sep. 17, 2002.

(51) Int. Cl.
*A61M 31/00* (2006.01)
*A62B 7/00* (2006.01)

(52) U.S. Cl. .............. 128/200.24; 128/204.18; 128/204.21; 128/204.23; 128/203.12

(58) Field of Classification Search ........... 128/200.24, 128/204.18, 204.21, 204.23, 204.22, 205.23; 600/529, 532, 530; 601/41
See application file for complete search history.

(56) References Cited

U.S. PATENT DOCUMENTS

| | | | |
|---|---|---|---|
| 2,918,917 A * | 12/1959 | Emerson | 128/205.19 |
| 4,463,756 A | 8/1984 | Thuc | |
| 5,555,880 A | 9/1996 | Winter et al. | |
| 5,893,361 A * | 4/1999 | Hughes | 128/200.24 |
| 6,058,932 A * | 5/2000 | Hughes | 128/200.24 |
| 6,085,746 A | 7/2000 | Fox | |
| 6,443,907 B1 * | 9/2002 | Mansy et al. | 600/529 |
| 6,640,807 B2 * | 11/2003 | Bennarsten | 128/205.24 |
| 7,000,610 B2 * | 2/2006 | Bennarsten et al. | 128/204.18 |
| 7,232,417 B2 * | 6/2007 | Plante | 601/46 |

* cited by examiner

*Primary Examiner*—Justine R Yu
*Assistant Examiner*—Clinton Ostrup
(74) *Attorney, Agent, or Firm*—Richard A. Ryan (57) ABSTRACT

The respiratory booster machine is configured to generate and transmit particularly designed and timely delivered vibrations to the lungs of a subject to improve ventilation, augment diffusion of gases across alveolar membrane, facilitate pulmonary blood perfusion, prevent focal alveolar collapse, and enhance effective expectoration. The machine has an acoustic signal generator having modulated wave-generating circuitry and an acoustic signal transmitter having an electro-acoustic transducer. Vibrations from the acoustic signal are induced into the subject's air stream, in one embodiment by a specially designed tube system, and then transmitted to a subject's airways via any type of endotracheal tube, respiratory mask, nasal prong, or directly through the chest wall. Acoustic signal receivers connected to a computer receive and analyze the effect of the vibrations on the subject. The machine can be used independently or in combination and cooperatively with any type of ventilator machine, either conventional or high frequency.

41 Claims, 7 Drawing Sheets

RESPIRATORY BOOSTER MACHINE AND METHOD FOR ENHANCING VENTILATION

CROSS-REFERENCE TO RELATED APPLICATIONS

This application claims the benefit of U.S. Provisional Application No. 60/411,167 filed Sep. 17, 2002.

BACKGROUND OF THE INVENTION

A. Field of the Invention

The field of the present invention relates generally to apparatuses and methods for improving and enhancing respiratory ventilation of live subjects. More particularly, the present invention relates to such apparatuses and methods which are capable of generating and transmitting vibrations to the lungs of a subject so as to augment diffusion of gases across the alveolar membrane, increase effective contact surface, prevent focal alveolar collapse, enhance effective expectoration and improve blood perfusion of the lungs. Even more particularly, the present invention relates to such apparatuses and methods which can be utilized independently or in combination and cooperatively with any type of ventilator machine.

B. Background

As is well known, the human body normally obtains the oxygen it needs to sustain life through a process of respiration or breathing that causes air to be inhaled and carbon dioxide to be exhaled through the mouth and nose. In the human body, the lungs are the organs that function to transmit oxygen from the inhaled air to the blood supply. The lungs have a plurality of successively branching bronchioles, essentially in the shape of an upside down tree, that are in gas exchange communication with the alveolar network of blood capillaries. The air obtained from respiration is transmitted from the alveoli to the capillaries. Due to injury, disease, prematurity, surgery or other circumstances, it can be necessary to provide respiratory assistance to a living subject.

Figure 1:
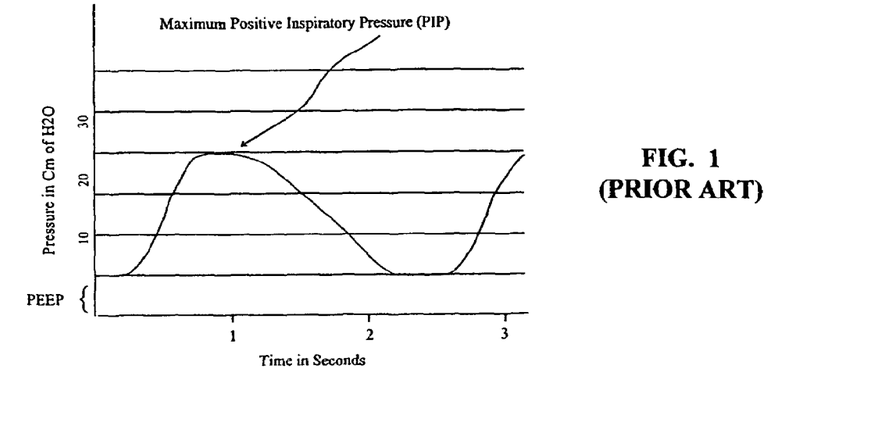
FIG. 1 is a graphical illustration of a CMV ventilator of the prior art.

In the field of medicine, conventional mechanical ventilators (CMVs) are utilized for ventilating the lungs of a patient who is either not able to breath on his or her own or who has respiratory failure of any cause. Typically, CMVs are configured to operate at tidal volumes, which is the amount of gas given with each breath, and frequency, which is the rate of the tidal volumes given in a minute, that approximate normal breathing patterns. For instance, a typical tidal volume for these machines is approximately 7 mL of gas for each Kg of body weight (7 ml/Kg), which is close to the 500 mL breathing volume that is normally expected of a 70 Kg healthy human being, and a typical rate can be 12-18 times per minute for an adult and 35-45 times per minute for a new-born. As a result, CMVs usually have a limit of up to 60 breaths per minute. The CMV provides a mixture of oxygen and air, or other breathable gases, to the patient at the necessary breath rates. Most CMVs can be fine tuned to the needs of the patient based on the fraction of inspired oxygen (FIO2) level, inspiration and expiration timing and volume/pressure limit settings. The typical CMV does not use negative pressure during exhalation, depending instead on the tendency of the lungs to deflate spontaneously. Often, some residual pressure is maintained during expiration, which is called positive end expiratory pressure (PEEP), in order to prevent collapse of the alveoli. A schematic representation of the way in which CMVs give breath to a subject is shown in FIG. 1.

Figure 2:
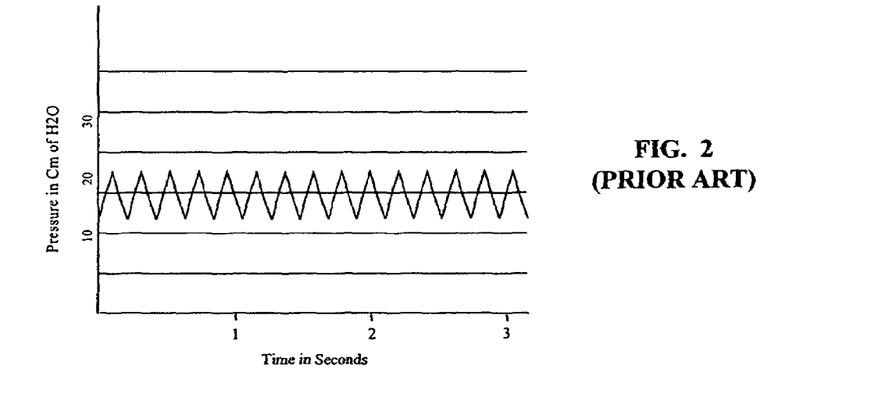
FIG. 2 is a graphical illustration of a HFOV ventilator of the prior art.
Figure 3:
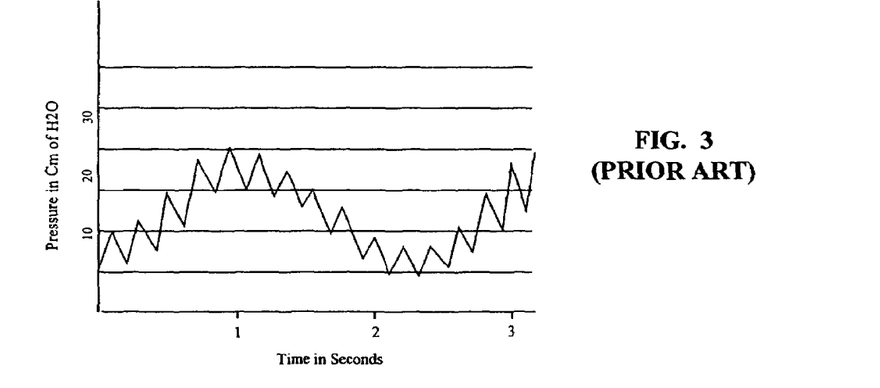
FIG. 3 is a graphical illustration of a combination ventilator of the prior art.

High frequency ventilators (HFV) were developed to provide the benefits of using higher breath rates in certain patients, particularly small neonates. These HFV machines use much higher respiratory rates combined with significantly lower tidal volumes (i.e., respiratory rates of 150-550 per minute and tidal volumes of 3-5 mL). Unfortunately, HFV machines were found to have the disadvantage of over-inflating the patient's lungs. Due to this problem and the emergence of active (negative pressure) expiration phase concepts, high frequency oscillatory ventilators (HFOV) were developed. A scheme of the way in which HFOV machines ventilate a patient's lungs is shown in FIG. 2. Other types of HFVs include combined conventional and high frequency ventilators, and the high frequency jet ventilator (HFJV), which uses multiple conduit endotracheal tubes and has the advantage of eliminating the dead-space of the proximal airways. Some of these more sophisticated machines are able to give a combination of high frequency small tidal volumes along with regular low rate breaths given by CMVs. A scheme of the way combination machines ventilate a patient's lungs is roughly shown in FIG. 3. Other types of HFVs are the high frequency fan ventilator (HFFV), high frequency flow interruption and high frequency chest wall oscillation.

Although not directly related to artificial ventilators, the bubble continuous positive airway pressure (Bubble CPAP) system is a relatively simple system that is suited for more stable patients. In this system, the inhaled gas passes through a sealed container half filled with water or like fluid prior to entering the subject's respiratory systems. In operation, a mixture of breathable gas enters the container through a first tube that has its tip submerged in the fluid and exits the container through a second tube that is sealed and secured to the lid of the container and configured to direct the breathable gas towards the patient. When the gas is pushed into the first tube with enough pressure, typically a few centimeters of water, bubbles result. The vibrations and/or subtle changes in the pressure of the inhaled gas created by the bubbles were found to improve the patient's oxygenation. The Bubble CPAP system, which is used in many hospitals nowadays with excellent results, illustrates the physiologic benefits of even a mild pressure oscillations on respiration. Bubble CPAP, however, cannot be used for patients who are unable to generate sufficient intrathoracic negative pressure to inhale a sufficient amount of breathable gas, despite the fact that positive pressure is given to the airways by the machine. The benefits of biologically variable (noisy) and stochastic ventilators for the treatment of respiratory distress syndrome (RDS) and atelectasis, as well as certain other respiratory conditions, is also well known and experienced.

The exact mechanism by which the HFV, stochastic noisy ventilator or bubble CPAP can improve a subject's oxygenation is not fully understood by those skilled in the art. It has been postulated that the vibrations from these machines are transmitted to the alveoli and quickly displace the gas immediately in contact with the alveolar membrane. These vibrations, or pulsations, also seem to be able to inflate the collapsed alveoli at lower pressures compared with CMV. The same strategy of generating intrathoracic vibrations is used in nature to augment respiration and oxygenation. Examples of such natural mechanisms are the crying of the newborn babies right after birth, grunting during sickness, groaning when in danger, growling in extreme anger and moaning during sexual intercourse.

One of the reasons why HFV works better than CMV might be the fact that minute volume (which is the amount of gas given to the lungs in one minute) is a more important parameter in ventilation of lungs than tidal volume. Although HFVs have tidal volumes equal or even less than the dead-space and, therefore, significantly less than the tidal volumes in CMVs, because breath rate in the HFV machine is significantly higher than CMV machine, the minute ventilation is remarkably higher in the HFV. As an example, in a 2 Kg baby on CMV with IMV rate of 40 per minute, minute volume would add up to approximately 560 mL (2×7×40=560). The same baby on a HFV will roughly receive 800-1200 mL of minute volume (assumming tidal volume of 2-3 mL and oscillation frequency of 400/min).

One of the major side effects of artificial ventilation of any kind is the development of chronic lung disease and life long morbidities. These side effects usually happen at higher pressures, higher FIO2, and prolonged ventilation. Therefore, it is highly desirable to use as low pressure and FIO2 setting for the shortest period possible. Because vibration of the alveolar membrane is the mainstay of improved respiration, and considering the fact that vibratory energy is known to dissipate along narrow tubes, in order to effectively improve respiration without being harsh on proximal airways it is necessary to use higher frequency vibrations. With higher frequency vibrations, it is possible to use lower pressures and milder oscillations to keep the alveoli open and rumbling, which is much less likely to result in damage to the lungs. Although the prior art discloses a variety of apparatuses and methods for enhancing ventilation of a human subject and despite the known or apparently known benefits of delivering vibratory energy to the lungs of a subject to improve oxygenation and decarbonization in health and sickness, no apparatus or method is known to beneficially and directly provide such vibratory effect to enhance ventilation, particularly the ability to effectively deliver these vibrations to terminal bronchioles and alveoli. Tests by the inventor indicate that the lower frequency vibrations generated by HFVs are not sufficient to deliver vibratory energy to terminal bronchioles and alveoli. It is postulated that frequencies of approximately 200-4000 Hz are necessary, depending on the size of the subject and/or his/her medical condition, to deliver the desired vibratory energy to the terminal bronchioles and alveoli. What is needed, therefore, is an apparatus and method of delivering vibrations to the lungs of a living subject without harming the airways and/or alveoli.

SUMMARY OF THE INVENTION

The respiratory booster machine and method for enhancing ventilation of the present invention provides the benefits and solves the problems identified above. That is to say, the present invention discloses an apparatus for improving alveolar gas exchange in the lungs of a living subject via augmented alveolar ventilation and perfusion, and enhanced diffusion of gases across alveolar membrane. The respiratory booster machine increases effective respiratory contact surface (the alveolar surface area that is in contact with the breathing gases) by vibrating the alveolar membranes. In addition, the respiratory booster machine facilitates re-opening of collapsed alveoli without the need to use potentially dangerous high positive inspiratory pressure (PIP). The simplicity of the respiratory booster machine and it's cost-effectiveness and broad applications in health and sickness makes this machine extremely useful. Use of wave frequencies above 20,000 Hz or ultrasound makes the machine silent to human ears, therefore less annoying to hospital staff, while retaining its beneficial effects on respiration. Even lower frequencies, such as in the range of 20-20,000 Hz, in the form of a monotone or a combination of band range (for example 40-200 Hz played along with 800-1400 Hz) or even musical wave formats is more tolerable to patients and hospital staff relative to the noise of HFOV or HFJV. Stochastic features of the respiratory booster machine in the form of breath-breath variations in intensity, frequency, and band-range combinations, make the machine more tolerable to the patient and staff, and less destructive to the lungs while improving alveolar expansion and defying atelectasis. The suitable tone, intensity, or musical quality of respiratory booster machine can be sought and implemented accordingly in light of the subject's weight, height, age and medical condition. Because the respiratory booster machine improves gas exchange, enhances circulation and facilitates the expelling of secretions and burst of formed bubbles, patients with disorders such as bronchiectasis, cystic fibrosis, adult respiratory distress syndrom (ARDS), chronic bronchitis, asthma, emphysema, pulmonary infarction, lung or sinus infections will benefit from its use.

In one aspect of the apparatus of the present invention, the respiratory booster machine has an acoustic signal generator configured to generate an acoustic signal, an acoustic signal transmitter operatively connected to the acoustic signal generator and in communication with a respiratory gas to induce the acoustic signal into the respiratory gas at or prior to the respiratory gas being absorbed in the lungs of a living subject, one or more acoustic signal receivers placed substantially adjacent to the living subject and configured to receive the acoustic signal in the living subject and a computing mechanism operatively connected to the acoustic signal receivers for analyzing the effect of the acoustic signal on the living subject's respiration. In the preferred embodiment, the acoustic signal transmitter has a sound emitting transducer disposed in an acoustic box with an acoustic funnel at one end that is connected to a ventilator's ventilation tube(s) via an adaptor so as to transmit the acoustic signal to the respiratory gas and therefore to the alveoli through the trachea, bronchi, bronchioles and eventually terminal bronchioles. The acoustic signal generator can incorporate modulated wave generating circuitry for generating the acoustic signal and/or be adapted to receive and play a sound such as the prerecorded cry of a baby, moaning, grunting or the like and/or even music thereon.

In another aspect of the apparatus of the present invention, the respiratory booster machine is incorporated directly into a ventilation apparatus for artificial respiration of a patient. As known in the prior art, the ventilator is connected to a source of respiratory gas so as to provide a pressurized gas stream to a patient through one or more ventilation tubes interconnecting the ventilator and the patient. The improved ventilator includes an acoustic signal generator for generating an acoustic signal and a computing means for analyzing the effect of the acoustic signal on the patient's respiration. Operatively connected to the signal generator is an acoustic signal transmitter that is configured to induce an acoustic signal from the acoustic signal generator into the respiratory gas prior to delivery of the pressurized gas stream to the patient. One or more acoustic signal receivers can be placed substantially adjacent the patient and configured to receive the acoustic signal in the patient and transmit that information to the computing mechanism to allow medical staff to analyze the respiration of the patient.

In one aspect of the method of the present invention, the method includes the steps of providing a pressurized respiratory gas stream from a ventilator connected to a supply of respiratory gas, generating an acoustic signal, inducing the acoustic signal into the pressurized respiratory gas stream, delivering the pressurized respiratory gas stream with the acoustic signal to the patient, monitoring the acoustic signal in the patient and analyzing the acoustic signal from the patient. As set forth above, the acoustic signal can be generated with an acoustic signal generator that is operatively connected to an acoustic signal transmitter for inducing the acoustic signal into the respiratory gas stream. The gas stream with the acoustic signal can be transmitted to the patient through an endotracheal tube in an intubated patient. One or more acoustic signal receivers can be placed substantially adjacent the patient and configured to receive the acoustic signal in the patient to accomplish the monitoring step. A computing mechanism, such as a computer, connected to the acoustic signal receivers can be used to accomplish the analyzing step.

Accordingly, the primary objective of the present invention is to provide a new respiratory booster machine and method of enhancing ventilation that provides the advantages described herein and that overcomes the disadvantages and/or limitations associated with presently available apparatuses and methods of enhancing respiration.

It is also an important objective of the present invention to provide a respiratory booster machine that enhances ventilation by transmitting an acoustic signal to the respiratory gases being inhaled by a living subject so as to cause vibration of the respiratory gases in the living subject prior to intake of the gases into the blood stream.

It is also an important objective of the present invention to provide a respiratory booster machine that enhances ventilation by transmitting an acoustic signal from an acoustic signal generator to ventilation tubes carrying pressurized air into a living subject (i.e., a patient) and utilizing one or more acoustic signal receivers placed substantially adjacent the living subject to receive the acoustic signal in the living subject so as to permit display and analyzation of these signals by a computer.

It is also an important objective of the present invention to provide a respiratory booster machine that enhances ventilation by utilizing a computer connected to one or more acoustic signal receivers to permit analyzation of the acoustic signals transmitted to a living subject with air from a ventilator.

It is also an important objective of the present invention to provide an improved ventilator that incorporates an acoustic signal generator to transmit acoustic signals to pressurized air from the ventilator and a computer to receive the acoustic signal from one or more acoustic signal receivers placed substantially adjacent to a living subject so as to enhance his or her ventilation.

It is also an important objective of the present invention to provide an improved method of artificial respiration that includes providing a respiratory gas stream, generating an acoustic signal, inducing the acoustic signal in the gas stream and then delivering the gas stream and acoustic signal to a living subject so as to enhance ventilation, improve pulmonary perfusion and augment diffusion of gases across alveolar membrane.

The above and other objectives of the present invention are explained in greater detail by reference to the attached figures and the description of the preferred embodiment which follows. As set forth herein, the present invention resides in the novel features of form, construction, mode of operation and combination of processes presently described and understood by the claims.

BRIEF DESCRIPTION OF THE DRAWINGS

In the drawings which illustrate the best modes presently contemplated for carrying out the present invention.

DETAILED DESCRIPTION OF THE PREFERRED EMBODIMENTS

With reference to the figures where like elements have been given like numerical designations to facilitate the reader's understanding of the present invention, and particularly with reference to the embodiments of the present invention illustrated in FIG. 4, the preferred embodiments of the present invention are set forth below. The enclosed figures and drawings are merely illustrative of the preferred embodiments and represent several different ways of configuring the present invention. Although specific components, materials, configurations and uses of the present invention are illustrated and set forth in this disclosure, it should be understood that a number of variations to the components and to the configuration of those components described herein and in the accompanying figures can be made without changing the scope and function of the invention set forth herein.

Figure 4:
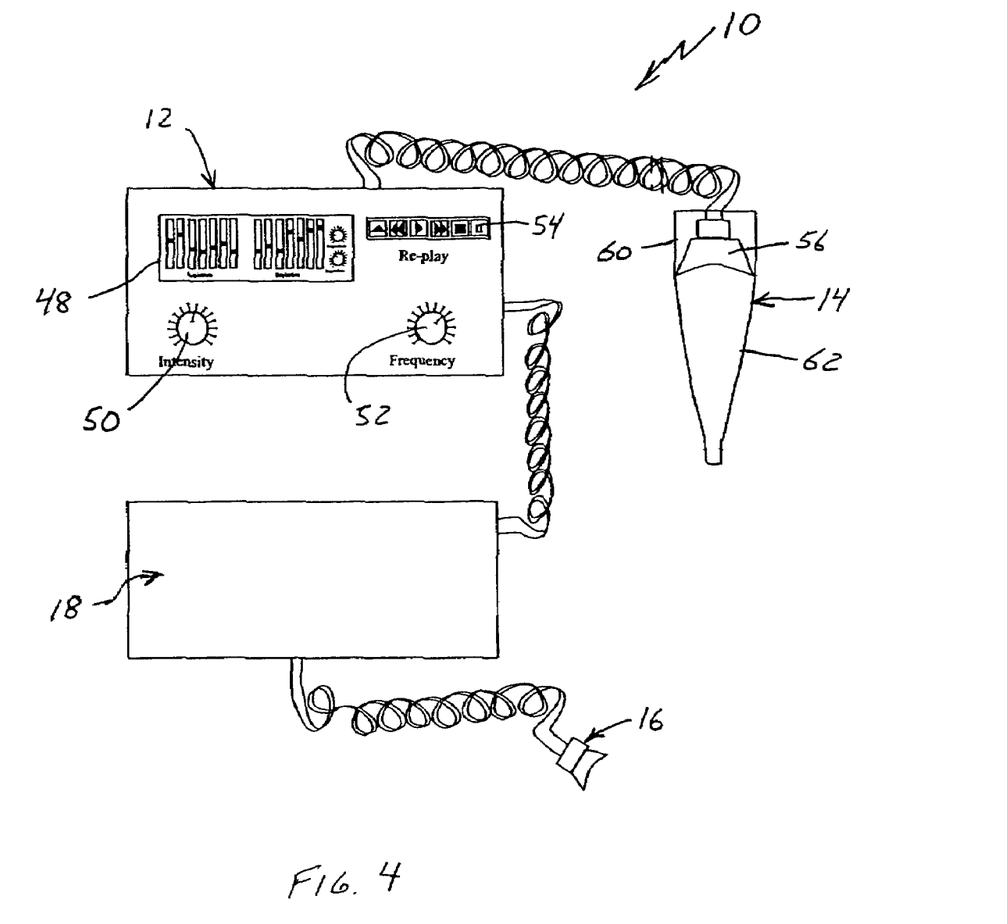
FIG. 4 is a schematic partial section view illustrating the major components of one embodiment of the respiratory booster machine of the present invention.
Figure 5:
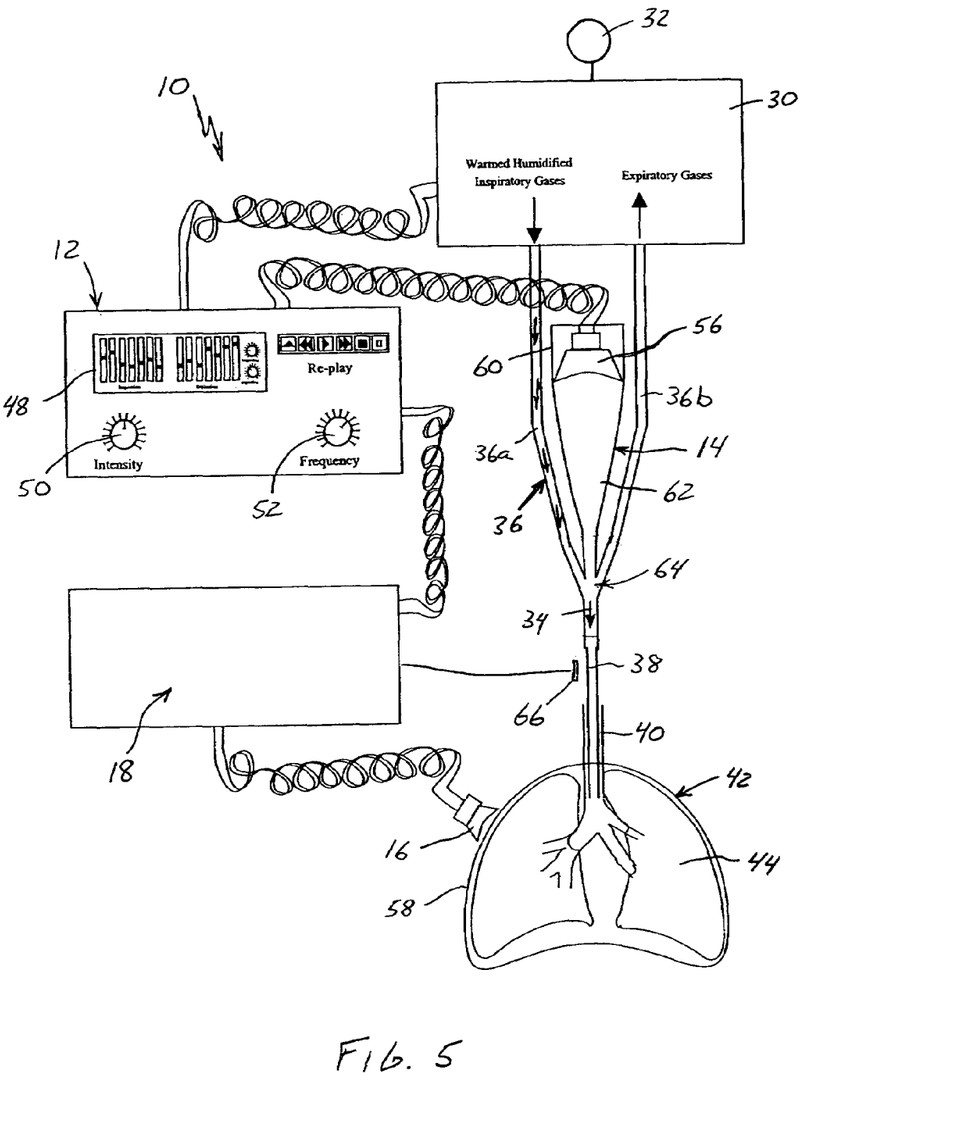
FIG. 5 is a schematic partial section view illustrating the major components of the embodiment of the respiratory booster machine of the present invention of FIG. 4 shown being used with a ventilator connected to a living subject.
Figure 6:
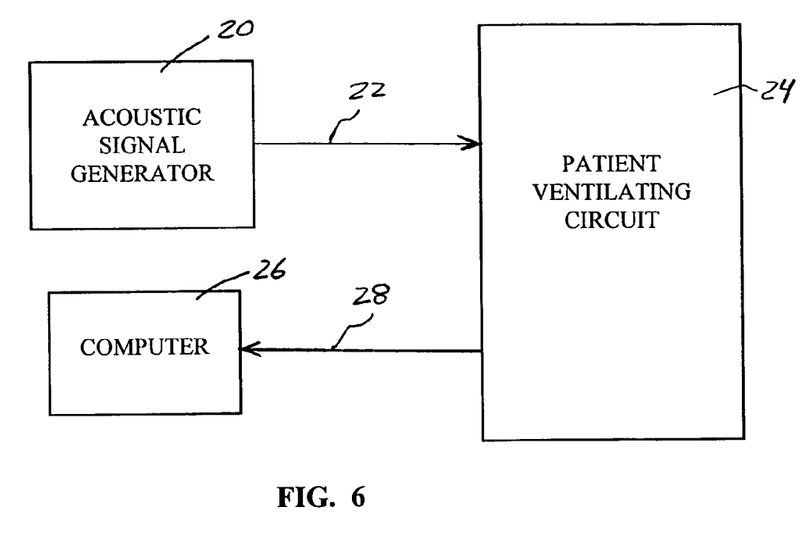
FIG. 6 is a circuit diagram of an embodiment of the respiratory booster machine in accordance with the present invention.
Figure 7:
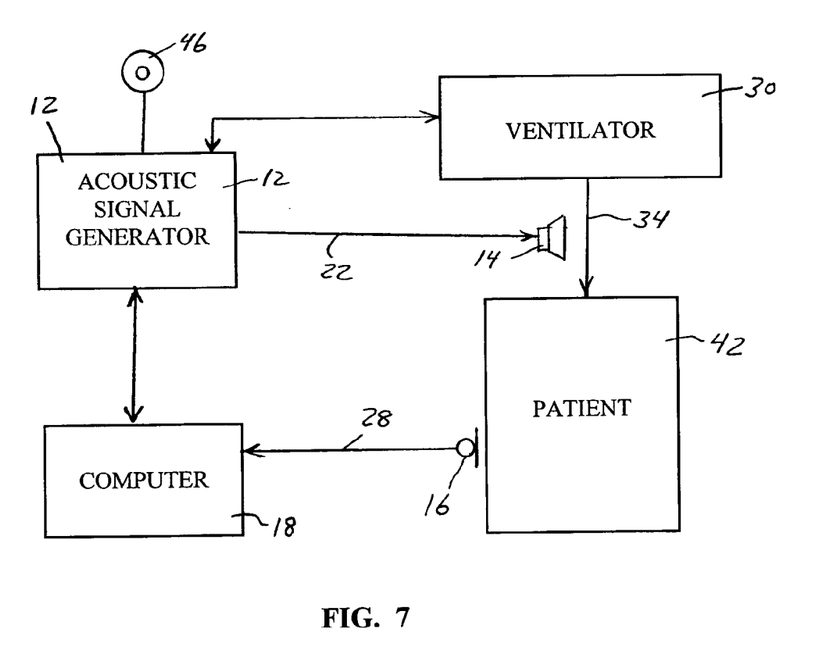
FIG. 7 is a circuit diagram of another embodiment of the respiratory booster machine in accordance with the present invention.
Figure 9:
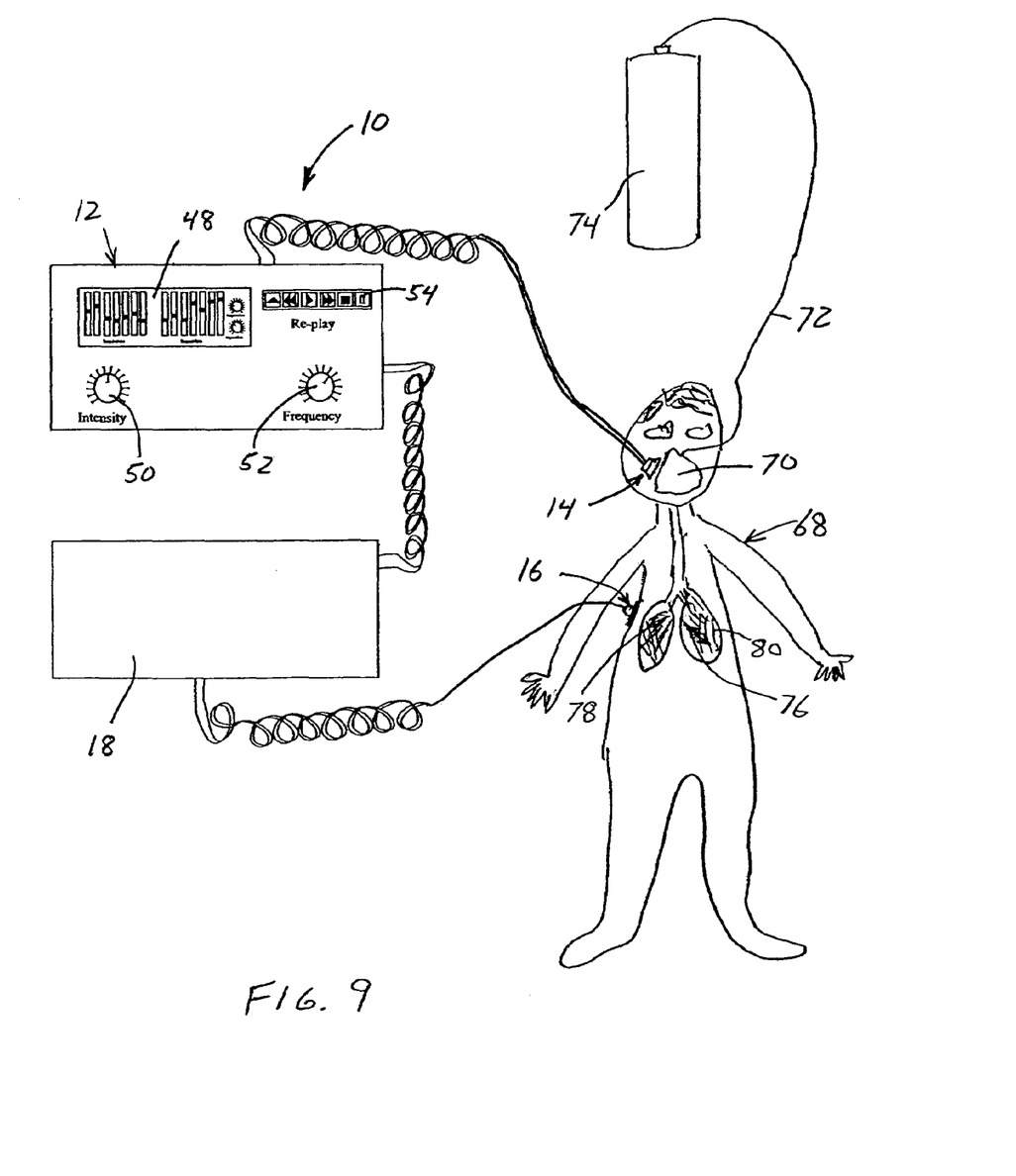
FIG. 9 a schematic partial section view illustrating the major components of another embodiment of the respiratory booster machine of the present invention shown connected to a living subject.

A preferred embodiment of the respiratory booster machine of the present invention, identified generally as 10 in the figures (as best shown in FIG. 4), primarily comprises an acoustic signal generator 12, an acoustic signal transmitter 14, one or more acoustic signal receivers 16 and computing mechanism 18. As shown in the schematic of FIG. 6, acoustic generating system 20, comprising signal generator 12 and signal transmitter 14, is configured to transmit an input acoustic signal, represented as 22, to a patient ventilating circuit 24, and acoustic receiving system 26, comprising signal receivers 16 and computing mechanism 18, is configured to receive an output acoustic signal, represented as 28, from the patient ventilating circuit 24. As shown in FIGS. 5 and 7, the typical patient ventilating circuit 24 primarily comprises a ventilator 30 connected to a supply of one or more respiratory gases 32 such as oxygen, air and/or other breathable gases and configured to provide an air or gas stream 34, (whether pressurized or not), one or more ventilator tubes 36, which can include inspiration tube 36a and an expiration tube 36b leading into and from ventilator 30, an endotracheal tube 38 configured for intubation in the trachea 40 of a patient 42 and configured for delivery of the gas stream 34 to the patient's lungs 44. As is known in the art, the gas stream 34 delivered to the lungs 44 facilitates artificial respiration of the patient 42 by encouraging gas exchange between the thin-walled alveoli 78 and the delicate capillaries 80 of the lungs 44 to provide oxygen for the patient's blood stream (as best shown in FIG. 9). As set forth in the background section above, ventilator 30 can be CMV, HFV, HFOV, HFJV or any other type of present or future ventilator or combinations of ventilators used to provide artificial respiration to a patient 42. The respiratory booster machine 10 of the present invention can also work with ventilators which generate negative pressure around the chest wall and, hence, cause inflow of gases into the trachea without the need for intubating the patient/subject.

Acoustic signal generator 12 of the preferred embodiment includes a modulated wave-generating circuitry capable of generating a wide range of electrical oscillations of variable frequency (usually 20-40,000) and intensity, as well as oscillations of protean, stochastic or musical quality. Acoustic signal generator 12 can include components for playing recorded sound and/or data that has been recorded on any type of sound media, exemplified by compact disk shown as 46 in FIG. 7, but which may include tapes, RAM technology, MP3, digital tapes and the like. This device can play the sound of a baby's cry, for example. To adjust for optimum resonance in the lungs of the patient, acoustic signal generator 12 may also include a single or multiple channel frequency equalizer, such as the two channel frequency equalizer 48 shown in FIG. 5 with an inspiration frequency equalizer and expiration frequency equalizer having controls 50 and 52 for the intensity level and frequency, respectively. Acoustic signal generator 12 may also have sound media controls 54 for controlling the playback of sound media 46. Power is supplied to acoustic signal generator 12 by AC, batteries or any other method appropriate for the particular type of acoustic signal generator utilized for respiratory booster machine 10 of the present invention.

Oscillations generated or retrieved from acoustic signal generator 12 are transmitted to acoustic signal transmitter 14 via wiring, as shown in FIG. 4, or wire-less technology (radio, infrared, etc.) or other methods known or to be developed. In the preferred embodiment, acoustic signal transmitter 14 includes electroacoustic transducer 56, such as a loud speaker composed of a diaphragm attached to a solenoid which is movable along a magnetic field, or other electroacoustic devices known in the relevant art. Alternatively, acoustic signal transmitter 14 can comprise piezoelectric technology, such as that used in some headphones or the transducer of an ultrasound machine. In general, acoustic signal transmitter 14 should be capable of playing mono-tone or variable/musical vibrations in a wide frequency range and be suitable for being engaged with, lodged onto or placed substantially adjacent to a respiratory mask, a nasal prong, a mouthpiece or any oral/nasal airway of any kind, any part of an endotracheal or nasal tube, or at the periphery of the chest wall 58 (identified in FIG. 7). In the preferred embodiment of the respiratory booster machine 10, the electroacoustic transducer 56 is encased inside an acoustic box 60 which can have a muffler (not shown) to reduce the noise for the patient 42 and medical staff. Preferably, acoustic box 60 extends into an acoustic funnel 62 on one side, as shown in FIG. 7. Acoustic funnel 62 is operatively connected to the patient's breathable gas entry port, for example endotracheal tube 38 via an airway adaptor 64, shown in FIG. 7, which is particularly configured to adapt to the type of ventilator 30 being used. For example, adaptor 64 will be different for HFOV compared with CMV or HFJV types of ventilators 30. In the preferred embodiment, acoustic funnel 62 has a disposable plastic lining (not shown) which could, depending on use, obviate the need for sterilization of acoustic funnel 62 after each use. In an easily portable embodiment of the invention, both acoustic signal generator 12 and acoustic signal transmitter 14 are encased in acoustic box 60.

As stated above, the one or more acoustic signal receivers 16 are configured to receive an output acoustic signal 28 from the lungs 44 of patient 42 resulting from the inspiration of gas stream 34 having input acoustic signal 22 (other than some noise loss, these are the same acoustic signal). In the preferred embodiment acoustic signal receiver 16 includes a microphone, as shown in FIGS. 4 and 5, that is placed substantially adjacent to chest wall 58 of patient 42. Acoustic signal receiver 16 is operatively connected to computing mechanism 18 so that it may receive, display and analyze, as desired, the various resonating frequencies in patient 42 so that an optimum intensity and frequency level may be set at acoustic signal generator 12. As with the acoustic signal transmitter 14, acoustic signal receiver 16 is operatively connected to computer mechanism via wiring, as shown in FIGS. 4 and 5, or wire-less technology (radio, infrared, etc.) or other methods known or to be developed. In one embodiment of the respiratory booster machine 10 of the present invention, one or more acoustic signal receivers 16 (i.e., relatively small, lightweight microphone devices) are placed on patient 42 at or about chest wall 58 so that they may pick-up the acoustic signal 22 resonating in various lobs of the subject's lungs 44. As known in the medical field, one or more microphones 16 can be incorporated into a chest strap-like device that goes around the chest wall 58 of patient 42.

Computer mechanism 18, which can include a conventional computer as shown in FIGS. 4 and 5, is configured to receive, display and analyze the output acoustic signal 28 received by the one or more acoustic signal receivers 16 at or near chest wall 58 of patient 42. To the extent desired by the manufacturers and/or operators of respiratory booster machine 10 of the present invention, computing mechanism 18 should be capable of at least analyzing the intensity and frequency of the retrieved acoustic signal 28 from various parts of the chest wall. Computing mechanism 16 can also include a display screen (not specifically shown) capable of displaying, in numeric and/or graphical form, information concerning the intensity and frequency of retrieved acoustic signal 28. In the preferred embodiment, shown in FIGS. 4 and 5, computing mechanism 16 operatively connects to acoustic signal generator 12 via wiring, as shown in the figures, or wire-less technology (radio, infrared, etc.), so that computing mechanism 16 may automatically, or as desired, adjust the intensity and frequency of the acoustic signal 22 output by acoustic signal generator 12 to provide an optimum or more optimum acoustic signal 22 to accomplish the objectives of the respiratory booster machine 10 of the present invention. As known by those skilled in the art, it is not necessary for computing mechanism 18 to be a separate computer or a "computer" at all. For instance, the functions of computing mechanism 18 can be incorporated into acoustic signal generator 12, with or without acoustic signal transmitter 14, or incorporated into ventilator 30 with or without acoustic signal generator 12. In addition, computing mechanism 18 can be any type of apparatus or device for receiving and analyzing intensity and/or frequency data from acoustic signal receiver 16. Measurement of noises from lungs 44 of patients 42 by respiratory booster machine 10 can also be used for calculating the lung's physical properties such as compliance or diagnose fluid accumulation or collapse of any of the lung lobes.

Figure 8:
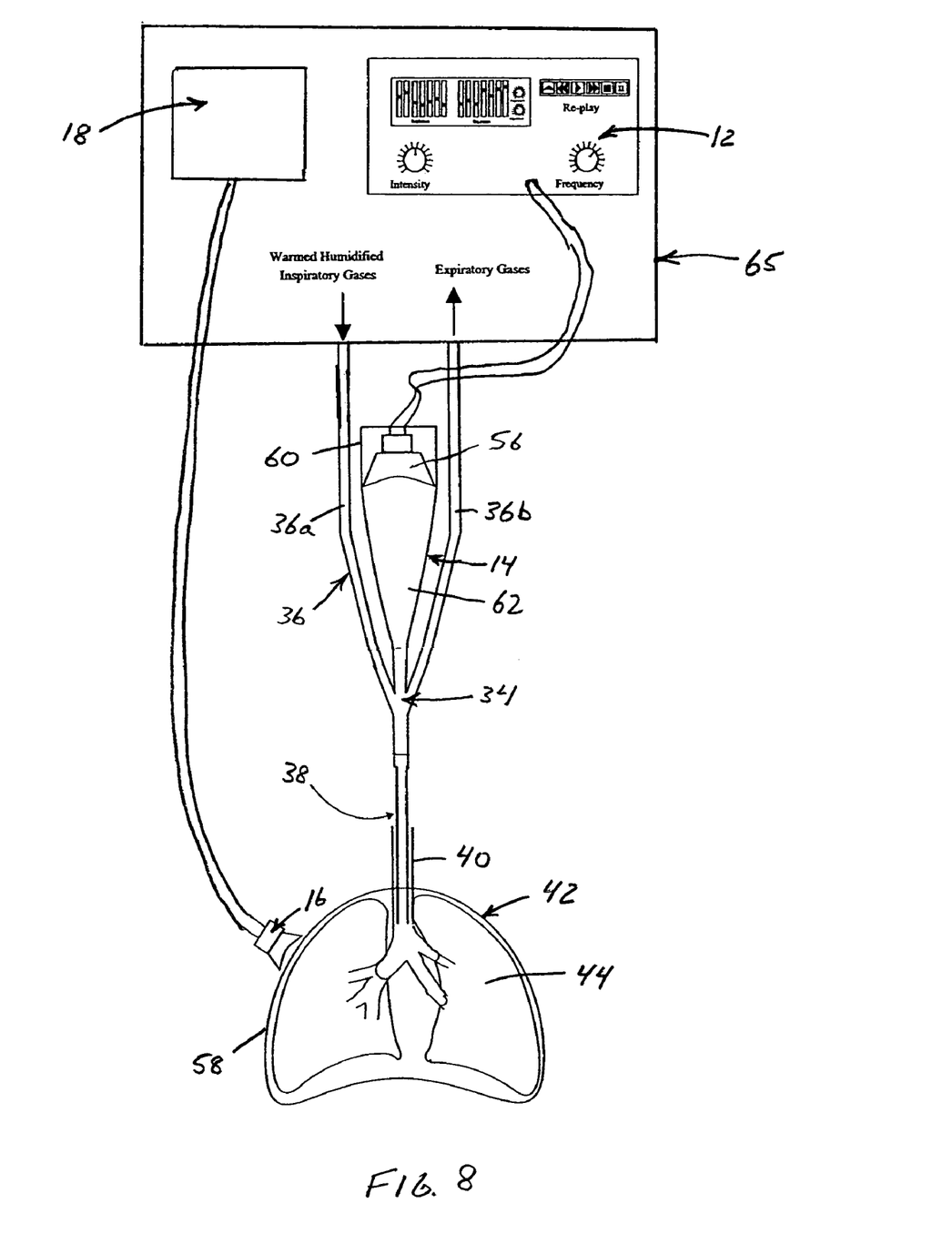
FIG. 8 is a schematic partial section view illustrating the embodiment of the present invention with the acoustic signal generator and computing mechanism incorporated into an improved ventilator.

As set forth above, acoustic signal respiratory generator 12 and/or computing mechanism 18 of respiratory booster machine 10 can be encased together within any type of present or future ventilator, shown as 65 in FIG. 8, to improve its function. As shown in FIG. 8, acoustic signal transmitter 14 and acoustic signal receiver 16 can connect to the respective functional components inside ventilator 65.

The oscillations generated by acoustic signal generator 12 can vary in frequency in relation to the time in the breath cycle, such that it can have a repetitive stochastic and even musical variation. For example oscillations of 500 Hz to be generated at the beginning of inspiration, 1000 Hz at the middle or end of inspiration, and frequencies as high as 4000-6000, or even higher, during expiration. Another set of frequencies with slightly different intensity can be used for the next breath cycle. In addition, the use of band range combinations may be able to help with some disease states and collapsed alveoli. The respiratory booster machine 10 improves oxygenation despite the lack of coordination between respiration cycles and oscillations (such as if a constant vibration of 700 Hz is generated). The desired frequency of the oscillations may well also depend on the size of the patient (i.e., usually the smaller the patient the higher the needed frequency) and also on the disease state, if any. The intensity of the oscillations is also subject to optional adjustment, meaning that the volume (in dB) of the noise made by the modulated wave-generating circuitry in the acoustic signal generator 12 or acoustic signal transmitter 14 and played by the electroacoustic transducer 56 can be adjusted. In one embodiment, respiratory booster machine 10 is able to reproduce the exact same cry for a new-born infant, for example, that is expected of the age and size of the subject.

As set forth above, in order to optimize the performance of respiratory booster machine 10, it is preferred to give variations in frequency and/or intensity of the vibrations on a breath-breath basis and also at any given time in any breath cycle. Therefore, pressure and/or flow sensors, shown generally as 66, can be located anywhere between the acoustic signal transmitter 14 and the endotracheal tube 38, in order to recognize patient 42 and/or ventilator 30 induced breaths and time slice in breath cycle. Sensors 66 can be connected to acoustic signal generator 12 or computing mechanism 18 and be configured to trigger the modulated wave-generating circuitry of the acoustic signal generator 12 for another breath cycle. In another embodiment of the invention, shown in FIG. 7, the wave-generating circuitry of acoustic signal generator 12 is operatively connected via wiring or wireless technology to the electronic board of ventilator 30 to receive the information from ventilator 30 regarding pressure, flow, I/E timing and etc., which may obviate the need for pressure/flow sensors 66.

As illustrated in FIG. 9, the apparatus 10 and method of the present invention can be utilized to improve respiration of a living subject 68 without the use of ventilator 30. Respiratory booster machine 10 can be adapted to operatively connect (i.e., by wire or wireless technology) to acoustic signal transmitter 14 at or near a typical respiratory mask 70 placed over the mouth of the living subject 68 (as shown), along the air tube 72 interconnecting respiratory mask 70 with a supply of air 74, such as oxygen, near or at the supply of air 74 itself or on or near the living subject 68, for instance near chest wall 58. In this configuration, acoustic signal transmitter 14 induces acoustic signal 22 into the air stream 34, whether pressurized or not, such that the air will carry the vibrations from acoustic signal 22 to assist in the gas exchange, shown as 76, between the alveoli 78 and capillaries 80 in the lungs 44 of the living subject 68. Acoustic signal transmitter only needs to induce acoustic signal 22 into the air stream prior to when gas exchange 76 takes place. Use of respiratory booster machine 10 in this manner will have an improved respiration benefit for divers, pilots, astronauts and others needing to breath supplemental air. Respiratory booster machine 10 and the method of the present invention can also be used with living subject 68 when no supplemental air is provided (i.e., when living subject 68 is breathing on his or her own through the mouth or nose). In this embodiment, the vibrations from acoustic signal 22 are imparted to the air breathed in by living subject 68 by placing one or more acoustic signal transmitters at or near the living subject's mouth, nose or chest prior to when gas exchange 76 takes place in lungs 44. The acoustic signal transmitter will induce the vibrations from acoustic signal 22 into the air stream, obtained by "normal" breathing, to provide the benefits described herein.

In use with a ventilator 30, the respiratory booster machine 10 of the present invention is configured to deliver an acoustic signal 22 from an acoustic signal generator 12 to an air stream 34 provided by ventilator 30. In one embodiment, shown in FIG. 5, an acoustic signal transmitter 13 is joined to one or more ventilating tubes 36 that deliver air stream 34 to patient 42. An airway adaptor 64, connected to the ventilating tube or tubes 36, is configured to facilitate transfer of acoustic signal 22 from acoustic signal transmitter 14 to air stream 34. In other embodiments, acoustic signal transmitter 14 can utilize alternative mechanisms to deliver acoustic signal 22 into air stream 34, whether pressurized or not. Air stream 34, with acoustic signal 22, is delivered to patient 42, i.e., via endotracheal tube 38, mask 70 or other devices well known in the medical field, such that it facilitates the gas exchange 76 between alveoli 78 and capillaries 80. One or more acoustic signal receivers 16 can be placed against patient 42 or close enough to patient 42 such that they can receive the acoustic signal 28 inside patient 42 to allow a computing mechanism 18 connected to acoustic signal receivers 16 to analyze the effect of acoustic signal 22 on the ventilation of patient 42. When the acoustic signal generator 12 and/or computing mechanism 18 components of respiratory booster machine 10 are incorporated into ventilator 65, ventilator 65 is used in the manner described above, just as single unit. When respiratory booster machine 10 is utilized without a ventilator 30, it is used in a similar manner, the primary difference being that the acoustic signal transmitter 14 transmits acoustic signal 22 to the non-ventilated or non-pressurized air through a mask, nose device or at the chest area of living subject 68.

Figure 10:
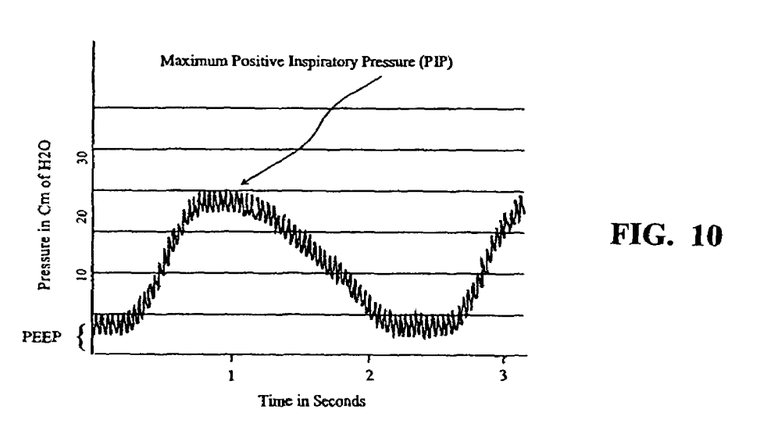
FIG. 10 is a graphical illustration of the effect of combining the respiratory booster machine of the present invention with a CMV ventilator.
Figure 11:
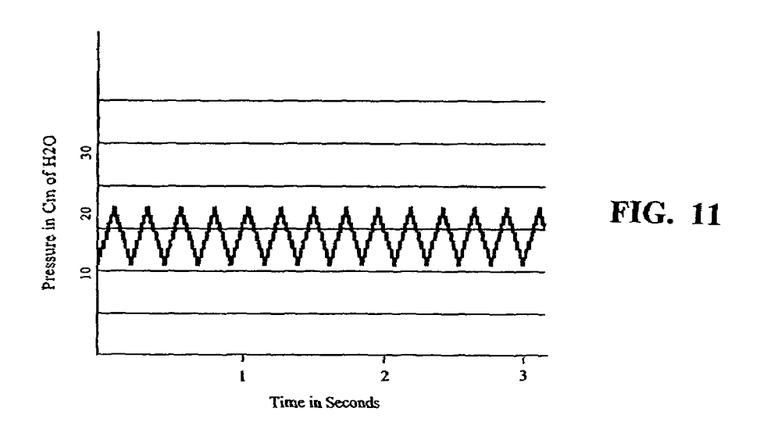
FIG. 11 is a graphical illustration of the effect of combining the respiratory booster machine of the present invention with a HFOV ventilator.
Figure 12:
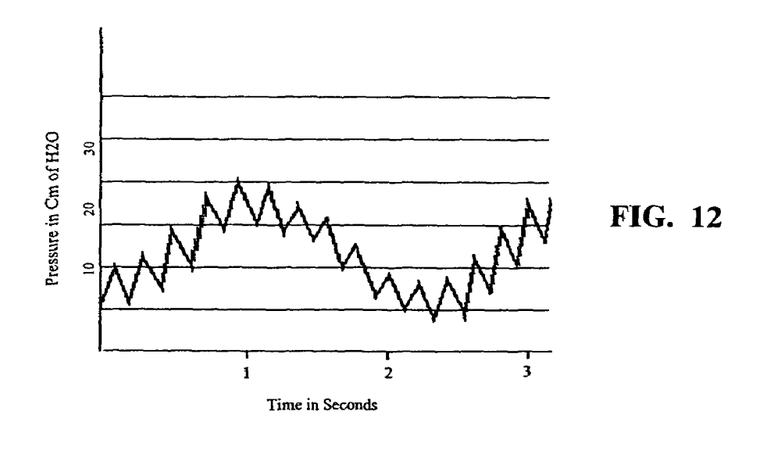
FIG. 12 is a graphical illustration of the effect of combining the respiratory booster machine of the present invention with a combination ventilator.

Until now high frequency ventilators have been using breathing cycles of up to 900 breaths per minute (9-15 Hz on most machines). High frequency jet ventilator (IMV of 660 Max) and some others are using a combination of conventional low rate (up to 60 breaths per minute) coupled with high frequency ventilations in order to improve oxygenation. Respiratory booster machine 10 of the present invention is capable of furthering oxygenation by adding another type of oscillation, very high frequency with very low tidal volume, which can transmit energy to the terminal bronchioles more efficiently. The way these very high frequency vibrations can be superimposed on CMV, HFOV or combined CMV and HFV ventilators are shown in FIGS. 10, 11 and 12, respectively. FIG. 10 illustrates the effect of combining respiratory booster machine 10 with a CMV ventilator, FIG. 11 illustrates the effect of combining respiratory booster machine 10 with a HFOV ventilator and FIG. 12 illustrates the effect of combining respiratory booster machine 10 with a combination ventilator. These ultra high frequency oscillations, coupled with artificial ventilation of any kind or used during normal breathing (in healthy subjects such as divers, astronauts, others), not only will enhance alveolar ventilation and re-opening of collapsed alveoli 78 but also will facilitate perfusion of gases through the alveolar membrane by virtually increasing the exchange area by means of vibrating the membrane and displacing the gas immediately in contact with the membrane. This is exemplified by grains sifting through a colander much faster when the sifter is shaken. Respiratory booster machine 10 of the present invention can be manufactured and encased together with any type of ventilator 30 to improve their efficacy. Respiratory booster machine 10 can also be manufactured so that it can be used in conjunction with older CMVs, HFVs, HFOVs, HFJVs, or any other type of present or future ventilators 30. Respiratory booster machine 10 can also be manufactured to be used without ventilator 30 such as for use under water, in space, for use at home or nursing homes, during recovery from any infectious or other disorder, for relief of fatigue, for leisure, or other purposes.

In disease states such as RDS or other similar respiratory problems where bubbles of air accumulate in the alveoli and impede effective respiration, the respiratory booster machine 10 of the present invention can be life saving. Experiments by the inventor indicate that the stochastic vibrations of respiratory booster machine 10 has a bursting effect on bubbles of air at a particular combination of vibrations, which cannot be achieved with just the higher inspiratory pressure setting on ventilators 30. Due to this effect, respiratory booster machine 10 can break apart bubbles formed in a patient's lungs 44. As a result, respiratory booster machine 10 can effectively help patients in such perilous medical conditions such as RDS and ARDS. In addition, tests also indicate that respiratory booster machine 10 of the present invention can improve expectoration in patients who can not effectively do the task through their biologic repertoire. This means that respiratory booster machine 10 can provide a benefit to those patients with cystic fibrosis, chronic bronchitis, bronchiectasis and the like, in addition to helping patients on prolonged artificial ventilation. In another embodiment of the present invention, referred to as a biologically active vibrator (BAV), the same vibrations will be applied to areas of the body having poor blood circulation, such as in sickle cell patients in vaso-occlusive crisis, and to augment local blood perfusion.

While there are shown and described herein certain specific alternative forms of the invention, it will be readily apparent to those skilled in the art that the invention is not so limited, but is susceptible to various modifications and rearrangements in design and materials without departing from the spirit and scope of the invention. For instance, it should be noted that the present invention is subject to modification with regard to the dimensional relationships set forth herein and modifications in assembly, materials, size, shape and use. In particular, the method and system of the present invention is adaptable to a wide variety of different types of ventilators and respiratory or other systems.

What is claimed is:

1. A respiratory booster machine to improve respiration of one or more respiratory gases by a living subject having a respiratory gas exchange between alveoli and capillaries in one or more lungs, said respiratory booster machine comprising: an acoustic signal generator configured to generate an acoustic signal; and an acoustic signal transmitter operatively connected to said acoustic signal generator and a patient ventilating circuit having a ventilator providing said one or more respiratory gases, said acoustic signal transmitter in communication with said one or more respiratory gases to transmit said acoustic signal into said one or more respiratory gases prior to said respiratory gas exchange between the alveoli and capillaries in said one or more lungs, said acoustic signal transmitter having an acoustic transducer capable of emitting audible and/or non-audible sound waves, said acoustic transducer disposed inside an acoustic box having an acoustic funnel, said acoustic funnel connected to one or more ventilation tubes to transmit said acoustic signal to said one or more respiratory gases prior to inhalation of said one or more respiratory gases by said living subject.

2. The respiratory booster machine according to claim 1 further comprising one or more acoustic signal receivers configured to be placed on or substantially adjacent said living subject so as to receive said acoustic signal in said living subject.

3. The respiratory booster machine according to claim 2 further comprising computing means operatively connected to said one or more acoustic signal receivers for analyzing the effect of said acoustic signal on said living subject.

4. The respiratory booster machine according to claim 1 further comprising computing means operatively connected to said acoustic signal generator and configured to adjustably control said acoustic signal generator to provide the desired or optimum intensity and frequency of said acoustic signal to said one or more respiratory gases.

5. The respiratory booster machine according to claim 1, wherein said acoustic funnel is operatively connected to an adaptor configured to join an inspiration tube and an expiration tube connected to said ventilator.

6. The respiratory booster machine according to claim 1, wherein said acoustic signal transmitter is operatively connected to an adaptor configured to join an inspiration tube and an expiration tube connected to said ventilator.

7. The respiratory booster machine according to claim 1, wherein said acoustic signal generator is operatively connected to said ventilator to permit functional interaction with said ventilator.

8. The respiratory booster machine according to claim 1, wherein said acoustic signal generator includes modulated wave generating circuitry for generating said acoustic signal.

9. The respiratory booster machine according to claim 1, wherein said acoustic signal generator is adapted to receive and play a sound media having recorded sound and/or data thereon.

10. The respiratory booster machine according to claim 1, wherein said acoustic signal is substantially the same sound intensity and frequency as that of a crying baby.

11. The respiratory booster machine according to claim 1, wherein said acoustic signal generator is adapted to transmit said acoustic signal to said one or more respiratory gases prior to inhalation of said one or more respiratory gases by said living subject.

12. A respiratory booster machine used with a patient ventilating circuit having a ventilator connected to a source of one or more respiratory gases to provide a gas stream to a patient with one or more ventilation tubes interconnecting said ventilator and said patient, said respiratory booster machine comprising: an acoustic signal generator configured to generate an acoustic signal; and an acoustic signal transmitter operatively connected to said acoustic signal generator and said patient ventilating circuit, said acoustic signal transmitter configured to induce said acoustic signal into said one or more respiratory gases prior to delivery of said gas stream to said patient, said acoustic signal transmitter having an acoustic transducer capable of emitting audible and/or non-audible sound waves, said acoustic transducer disposed inside an acoustic box having an acoustic funnel, said acoustic funnel connected to said one or more ventilation tubes to transmit said acoustic signal to said pressurized gas stream.

13. The respiratory booster machine according to claim 12, wherein said gas stream is pressurized.

14. The respiratory booster machine according to claim 12 further comprising one or more acoustic signal receivers configured to be placed on or substantially adjacent said patient so as to receive said acoustic signal in said patient.

15. The respiratory booster machine according to claim 14 further comprising computing means operatively connected to said one or more acoustic signal receivers for analyzing the effect of said acoustic signal on said patient.

16. The respiratory booster machine according to claim 12 further comprising computing means operatively connected to said acoustic signal generator and configured to adjustably control said acoustic signal generator to provide the desired or optimum intensity and frequency of said acoustic signal to said one or more respiratory gases.

17. The respiratory booster machine according to claim 12, wherein said acoustic funnel is operatively connected to an adaptor configured to join an inspiration tube and an expiration tube connected to said ventilator.

18. The respiratory booster machine according to claim 12, wherein said acoustic signal transmitter is operatively connected to an adaptor configured to join an inspiration tube and an expiration tube connected to said ventilator.

19. The respiratory booster machine according to claim 12, wherein said acoustic signal generator is operatively connected to said ventilator to permit functional interaction with said ventilator.

20. The respiratory booster machine according to claim 12, wherein said acoustic signal generator includes modulated wave generating circuitry for generating said acoustic signal.

21. The respiratory booster machine according to claim 12, wherein said acoustic signal generator is adapted to receive and play a sound media having recorded sound and/or data thereon.

22. The respiratory booster machine according to claim 12, wherein said acoustic signal generator includes one or more controls for controlling the intensity and/or frequency of said acoustic signal.

23. A ventilation apparatus for artificial respiration of a patient, said ventilation apparatus comprising: a ventilator connected to a source of one or more respiratory gases to provide a gas stream to said patient through one or more ventilation tubes interconnecting said ventilator and said patient, said ventilator having an acoustic signal generator for generating an acoustic signal and a computing means for analyzing the effect of said acoustic signal; an acoustic signal transmitter operatively connected to said acoustic signal generator and configured to induce an acoustic signal from said acoustic signal generator into said respiratory gases prior to delivery of said gas stream to said patient, said acoustic signal transmitter having an acoustic transducer capable of emitting audible and/or non-audible sound waves, said acoustic transducer disposed inside an acoustic box having an acoustic funnel, said acoustic funnel connected to said one or more ventilation tubes to transmit said acoustic signal to said pressurized gas stream; and one or more acoustic signal receivers configured to be placed on or substantially adjacent said patient and configured to receive said acoustic signal in said patient, said one or more acoustic signal receivers operatively connected to said computing means.

24. The respiratory booster machine according to claim 23, wherein said one or more ventilation tubes includes an inspiration tube, an expiration tube and a endotracheal tube for intubation in said patient, said acoustic funnel operatively connected to an adaptor configured to join said inspiration tube and said expiration tube to said endotracheal tube.

25. The respiratory booster machine according to claim 23, wherein said one or more ventilation tubes includes an inspiration tube and an expiration tube, said acoustic signal transmitter operatively connected to an adaptor configured to join said inspiration tube and said expiration tube.

26. The respiratory booster machine according to claim 23, wherein said computing means is operatively connected to said acoustic signal generator and configured to adjustably control said acoustic signal generator so to provide the desired or optimum intensity and frequency of said acoustic signal to said respiratory gases.

27. The respiratory booster machine according to claim 23, wherein said acoustic signal generator includes modulated wave generating circuitry for generating said acoustic signal.

28. The respiratory booster machine according to claim 23, wherein said acoustic signal generator is adapted to receive and play a sound media having recorded sound or data thereon.

29. The respiratory booster machine according to claim 23, wherein said acoustic signal is substantially the same sound intensity and frequency as that of a crying baby.

30. A method of improving respiration of one or more respiratory gases by a living subject having a respiratory gas exchange between alveoli and capillaries in one or more lungs, said method comprising the steps of:
  a) generating an acoustic signal with an acoustic signal generator having an acoustic signal transmitter operatively connected thereto, said acoustic signal transmitter having an acoustic transducer capable of emitting audible and/or non-audible sound waves, said acoustic transducer disposed inside an acoustic box having an acoustic funnel; b) providing said one or more respiratory gases through one or more ventilation tubes connected to a ventilator, said ventilator operatively connected to said acoustic signal generator: and c) inducing said acoustic signal from said acoustic funnel into said one or more respiratory gases with said acoustic signal transmitter prior to said respiratory gas exchange between the alveoli and capillaries in said one or more lungs, said acoustic funnel connected to said one or more ventilation tubes to transmit said acoustic signal to said one or more respiratory gases.

31. The method according to claim 30, wherein said acoustic signal transmitter is configured to transmit said acoustic signal into a pressurized respiratory gas stream configured to deliver said one or more respiratory gases to said one or more lungs.

32. The method according to claim 30 further comprising the step of delivering said respiratory gas stream with said acoustic signal to said living subject after said inducing step.

33. The method according to claim 32, wherein said delivering step is accomplished with an endotracheal tube intubated in said living subject.

34. The method according to claim 30 further comprising the step of monitoring said acoustic signal in said living subject after said inducing step.

35. The method according to claim 34, wherein said monitoring step includes one or more acoustic signal receivers placed on or substantially adjacent said living subject and configured to receive said acoustic signal in said living subject.

36. The method according to claim 35, wherein said one or more acoustic signal receivers are operatively connected to a computing means for analyzing the effect of said acoustic signal on said living subject.

37. A method of improved artificial respiration of a patient, said method comprising the steps of: a) providing a pressurized respiratory gas stream through one or more ventilation tubes from a ventilator connected to a supply of one or more respiratory gases; b) generating an acoustic signal with an acoustic signal generator having an acoustic signal transmitter operatively connected thereto, said acoustic signal generator operatively connected to said generator, said acoustic signal transmitter having an acoustic transducer capable of emitting audible and/or non-audible sound waves, said acoustic transducer disposed inside an acoustic box having an acoustic funnel, said acoustic funnel connected to said one or more ventilation tubes; c) inducing said acoustic signal into said pressurized respiratory gas stream by transmitting said acoustic signal from said acoustic funnel; d) delivering said pressurized respiratory gas stream with said acoustic signal to said patient; e) monitoring said acoustic signal in said patient; and f) analyzing said acoustic signal from said patient.

38. The method according to claim 37, wherein said delivering step is accomplished with an endotracheal tube intubated in said patient.

39. The method according to claim 37, wherein said monitoring step is accomplished with one or more acoustic signal receivers placed on or substantially adjacent said patient and configured to receive said acoustic signal in said patient.

40. The method according to claim 39, wherein said analyzing step is accomplished with a computing means operatively connected to said one or more acoustic signal receivers, said computing means configured for analyzing the effect of said acoustic signal on said patient.

41. The method according to claim 37, wherein said analyzing step is accomplished with a computing means.

\* \* \* \* \*